United States Patent [19]

Foster

[11] 4,331,143
[45] May 25, 1982

[54] ENDOTRACHEAL TUBE HOLDER

[76] Inventor: Billy R. Foster, 1040 Glen Common, Livermore, Calif. 94550

[21] Appl. No.: 167,419

[22] Filed: Jul. 11, 1980

[51] Int. Cl.³ .............................................. A61M 25/00
[52] U.S. Cl. ........................... 128/207.17; 128/207.14; 128/DIG. 26
[58] Field of Search .................... 128/207.14, 207.17, 128/207.18, 207.13, DIG. 26, 283, 206.14, 206.25

[56] References Cited

U.S. PATENT DOCUMENTS

| | | | |
|---|---|---|---|
| 2,831,487 | 4/1958 | Tafilaw | 128/DIG. 26 |
| 3,046,989 | 7/1962 | Hill | 128/207.18 |
| 3,774,616 | 11/1973 | White et al. | 128/207.14 |
| 3,924,636 | 12/1975 | Addison | 128/DIG. 26 |
| 3,946,742 | 3/1976 | Eross | 128/DIG. 26 |
| 3,972,321 | 8/1976 | Proctor | 128/DIG. 26 |
| 3,987,798 | 10/1976 | McGinnis | 128/207.15 |
| 4,114,626 | 9/1978 | Beran | 128/DIG. 26 |
| 4,192,785 | 3/1980 | Chew et al. | 128/283 |

Primary Examiner—Henry J. Recla
Attorney, Agent, or Firm—Francis H. Lewis

[57] ABSTRACT

An endotracheal tube holder includes a thin contoured plate fitting over the patient's nose with openings for the nostrils, a supporting member extending downward from the nose plate, and a tube holder attached to the supporting member having a C-shaped channel into which the endotracheal tube may be inserted laterally and held firmly in place by the walls of the channel. The contoured plate is held in place by an elastic strap attached to either side of the plate and extending around the back of the patient's head. A pair of supplemental elastic straps are attached to the supporting member, the opposite ends being fastened to the first strap at locations near the middle of either cheek. The supplemental straps pass through small constricting openings in the main strap at these locations, being squeezed and frictionally fastened to the main strap, and they may be tightened by pulling them through the openings.

10 Claims, 5 Drawing Figures

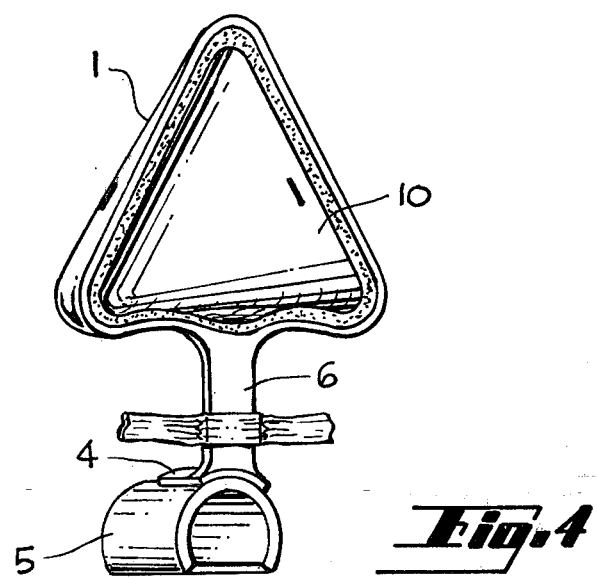

ENDOTRACHEAL TUBE HOLDER

BACKGROUND OF THE INVENTION

1. Field of the Invention

This invention pertains generally to the field of medical and surgical devices, and more particularly to the field of devices for holding or supporting endotracheal tubes during medical treatment or surgery.

2. Description of the Prior Art

During medical treatment or surgery it is often necessary to provide an unobstructed passage or airway to the patient's lungs to administer oxygen or to facilitate breathing. This problem arises especially during acute situations involving blockage of the mouth, throat or tracheal passage by blood, mucus, or other foreign material. The problem is solved by insertion of an endotracheal tube through the patient's mouth and into the trachea to provide a free flow of air or oxygen. This tube must be maintained in its proper position for extended periods of time. It is desirable to provide means other than manual for holding this tube in place so that the surgeon's or technician's hands are free for other activities during treatment.

A common and typical method for maintaining the position of the endotracheal tube is by means of adhesive tape placed over the patient's mouth and wrapped around the tube. This traditional method is inconvenient and time consuming, and suffers from several drawbacks. Generally a considerable amount of tape is required, and in medical emergency situations valuable time must be spent taping the tube in place. Once the tube has been secured by this method it will remain in place only temporarily, because sweat, saliva, blood, or other secretions are absorbed by the adhesive tape, causing it to loosen and allowing the tube to become displaced. Therefore the tape must be removed periodically and fresh tape must be applied. Even when fresh adhesive tape is used, considerable skill is required to wrap the tape in such a manner as to hold the tube immobile because of the inherent flexibility of the tape. Further, the adhesive tape obstructs the patient's mouth so that blood or other foreign fluids cannot be removed by a suction tube while the endotracheal tube is in place, unless the suction tube is also rendered immobile by the tape and both tubes are installed simultaneously. Finally, this use of adhesive tape causes considerable discomfort to the patient.

Several devices have been developed in the past to attempt to overcome some of these and other drawbacks of the adhesive tape method for supporting endotracheal tubes. One typical device is disclosed in U.S. Pat. No. 3,774,616 (White, et al.) which teaches an endotracheal tube holder fastened to a face plate, bite block and airway fitting into and over the patient's mouth. The entire configuration is held in place by an adjustable strap passing around the patient's upper neck. This use of a bite block has several disadvantages, in that tearing of gum tissue and trauma to the interior of the patient's mouth may be caused. The bite block and airway must be inserted over the patient's tongue; however, the face plate restricts the access of a tongue depressor to the corners of the patient's mouth, and hinders this insertion. Also, the position of the strap around the patient's neck is such that it can be dislocated and the tube holder may be dislodged by involuntary motion or spasms of the patient's head.

A similar face-plate device without the bite block and airway is disclosed in U.S. Pat. No. 3,924,636 (Addison). This device and the White device share the disadvantage that access to the patient's mouth is restricted by the face plate. Both devices are unsuitable for medical emergency room applications for this reason. In addition, this device employs a plastery adhesive to fasten the face plate over the patient's mouth, and thus it encounters many of the problems associated with the use of adhesive tape.

U.S. Pat. No. 3,946,742 (Eross) discloses an endotracheal tube holder having a short C-shaped bite member and tube retainer, movably fastened by an arm to an adjustable strap passing around the patient's chin and the back of the upper neck. The tube retainer arm rests against the patient's chin, generally causing discomfort and trauma. Accordingly, the position of the arm must be changed periodically. This device has been found unsatisfactory in many instances because it does not hold the tube firmly in place but allows it to shift position in all directions in the patient's mouth. The commercially available version of this device is provided with an additional stabilizing chin strap (not disclosed in the above patent), but this chin strap is unsuitable for patients with dentures. Further, this device is awkward and difficult to adjust and fasten quickly to an emergency room patient who is moving involuntarily.

SUMMARY OF THE INVENTION

The improved endotracheal tube holder disclosed herein provides a rigid support member shaped to fit over the firm ridge of the patient's nose with cutout openings for the nostrils. This member includes an L-shaped arm extending downward from the nose and outward from the upper lip. The arm is attached to a short tube holder of semi-rigid plastic material directly in front of the patient's mouth. The holder is in the shape of a hollow cylindrical section with a longitudinal strip of the wall removed, such that its cross section is approximately C-shaped, allowing the tube to be snapped laterally in place into the holder. The support member is held in place over the patient's nose by an elastic strap extending around the back of the head with ends attached to the support member on either side of the nose. A second pair of elastic stabilizing straps are attached to either side of the L-shaped arm, with their opposite ends fastened to the firt elastic strap at points along the two sides of the patient's head near the center of the cheek. These second straps pass through small constricting holes in the first strap; the ends, being knotted, when pulled cause the straps to tighten.

It is an object of this invention to provide an endotracheal tube holder which will maintain the tube firmly and stably in its proper position while the patient's head and jaw undergo rapid or spasmodic motions, without any readjustment or re-positioning of the tube holder being necessary.

A second object of this invention is to provide an endotracheal tube holder which allows maximum access to the patient's mouth while the tube is in place.

Another object of this invention is to provide an endotracheal tube holder which may be rapidly and easily applied to the patient without requiring any substantial adjustments.

Another object of this invention is to provide an endotracheal tube holder which will not cause any unnecessary injury or trauma to the patient's mouth, or other discomfort to the patient.

A further object of this invention is to provide an endotracheal tube holder which will maintain its position for extended periods of time, without any necessity for re-positioning or readjustment.

These and other objects, advantages, characteristics and features of this invention may be better understood by examining the following drawings together with the detailed description.

BRIEF DESCRIPTION OF THE DRAWINGS

FIG. 4 is a pictorial view of the tube holder showing the rear surfaces.

FIG. 5 is a front elevational view of the tube holder constructed in an alternative form, shown in position for use on a patient.

DETAILED DESCRIPTION OF THE PREFERRED EMBODIMENT

Figure 1:
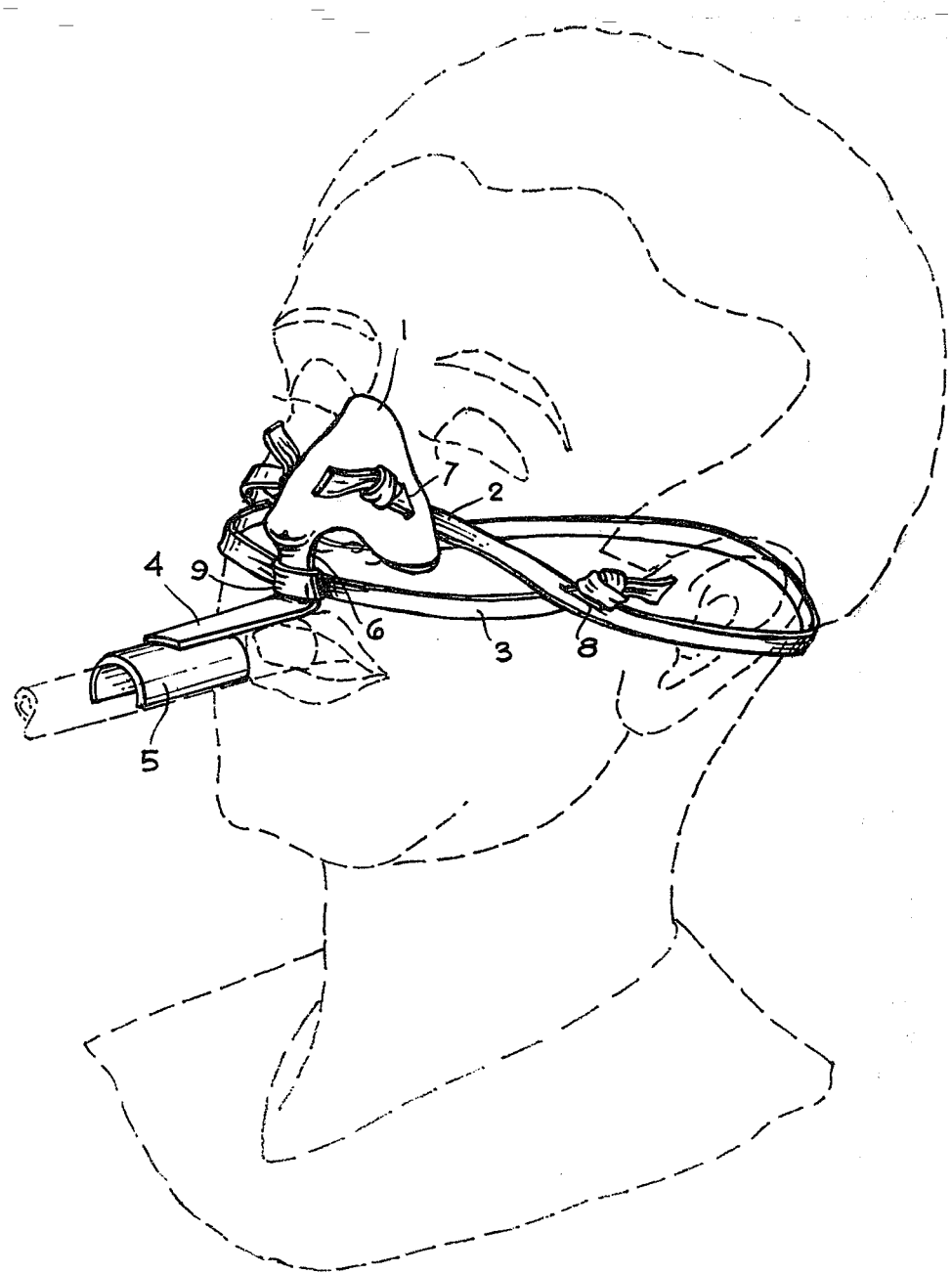
FIG. 1 is a perspective view of the endotracheal tube holder according to the present invention positioned on a patient, holding an endotracheal tube.
Figure 2:
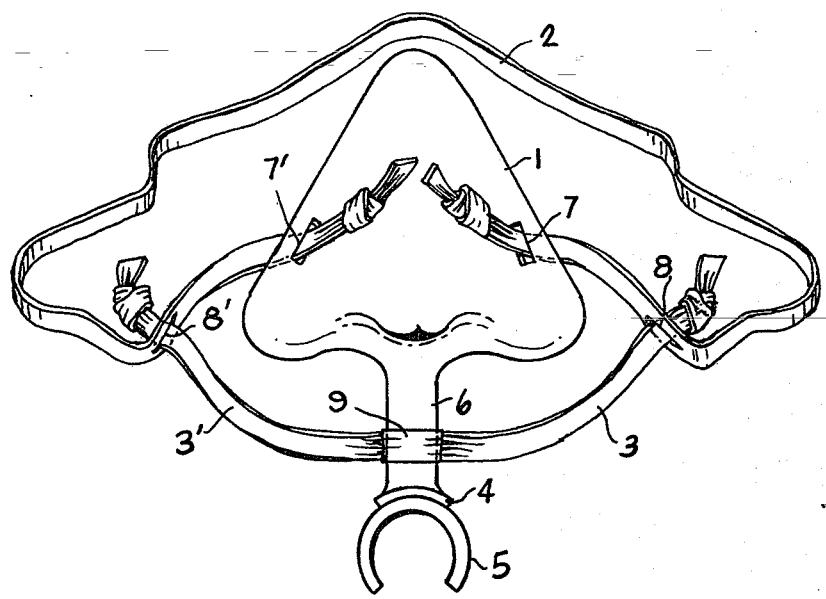
FIG. 2 is a front elevational view of the tube holder.
Figure 3:
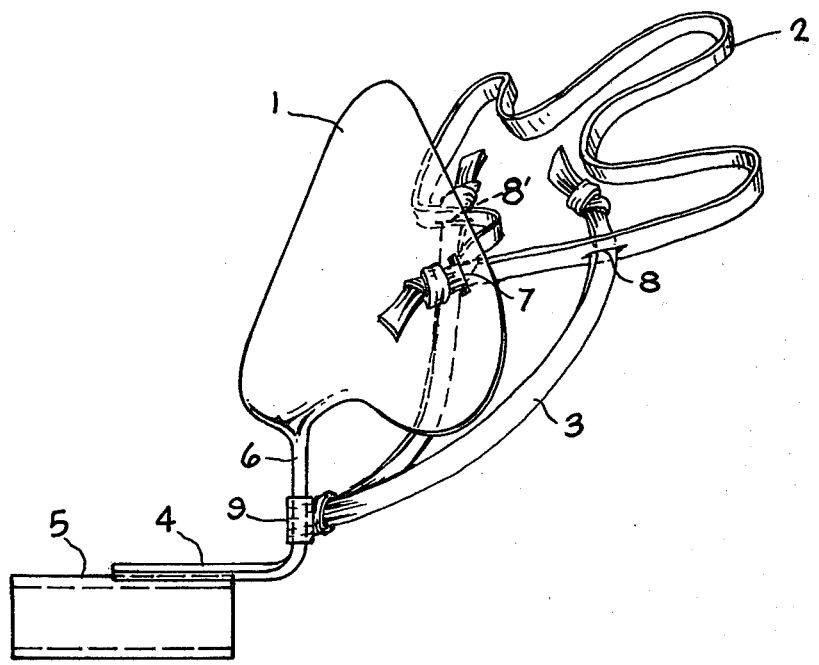
FIG. 3 is a side view of the tube holder.

Referring to the drawings, the endotracheal tube holder includes a thin support plate member 1 which is shaped to fit over the nose of the patient, with indentations cut out along its lower edge to provide openings for the nostrils. This support member is connected to an elastic strap 2, the ends of which are attached to each side of the support member at openings 7 located approximately midway between the top and bottom of the support member near its outer lateral edges. The support member is fabricated preferably from light inexpensive material, sufficiently flexible to readily conform to the contour of the patient's face, such as plastic or similar material. The inner surface of this support member may be lined with a thin layer of soft absorbent material 10, such as gauze or the like, to absorb sweat from the patient's skin and provide maximum comfort. This lining may be glued to the support member surface.

The lower portion of the support member 1 extends over the end of the patient's nose into a narrow flat strip 6 underneath, and projecting downward from, the septum between the patient's nostrils. This strip is preferably bent into an L-shape, so that its lower portion forms a flat horizontal arm 4 extending outward from the patient's upper lip. The vertical portion 6 of this strip rests in place against the skin surface between the upper lip and the lower extremity of the nasal septum.

The lower surface of the horizontal arm 4 is rigidly fastened to the tube support 5. This tube support comprises a short open-ended thin-walled C-shaped channel, the axis of the channel being parallel to the horizontal arm 4 and disposed below it to point directly into the patient's mouth. The channel is of proper size and location to accommodate an endotracheal tube along the channel axis passing into the patient's mouth. The walls of the channel extend sufficiently far around and grip the outer surface of the endotracheal tube to hold it firmly in place during use. The open lateral side of the C-shaped channel extends its full length, and the channel is formed of stiff plastic material with sufficient resilience to allow the endotracheal tube to be laterally inserted and snapped into place in the channel. As shown in the drawings, the open lateral edges of the channel comprise the lower extremity of the tube support. The tube support 5 is attached to the horizontal arm 4 by means of glue or other similar fastening means well-known to persons skilled in the relevant art to which this invention pertains.

Referring still to the drawings, short elastic straps 3, 3' of equal length are attached to the vertical narrow flat strip 6 approximately at its midpoint elevation. The opposite ends of these short elastic straps are fastened to the elastic strap 2 respectively on each side of the support member 1 at points 8, 8' which lie approximately at the middle of the patient's cheeks when the tube holder is in place. The straps 3, 3' pass through small openings 8, 8' in the strap 2 frictionally securing said straps, with knotted ends. They are tightened by pulling them through said openings to secure the lower portion of the support member. The elastic strap 2 is of proper length to allow it to fit over and around the patient's head only when it is stretched, thereby similarly providing firm stable lateral support to the upper portion of the support member. As shown in FIG. 1, with the tube holder in place the stretched elastic strap 2 fits around the patient's head at a position slightly below the ears.

From the above description it will be understood that the tube holder may be emplaced in position on the patient after intubation of the endotracheal tube. It will be further seen that the endotracheal tube may be removed, replaced, or adjusted without removing, adjusting, or otherwise disturbing the tube holder. The position and stability of the emplaced tube holder are unaffected by movements of the patient's head, mouth, or jaw. The tube holder allows maximum access to the patient's mouth while emplaced, and does not induce any trauma or injury to the mouth during emplacement or use. The use of elastic straps obviates the need for any adjustment other than simply tightening the lower straps, and allows rapid emplacement.

It will be further appreciated that various modifications and changes may be made in the above-described endotracheal tube holder while preserving the features and advantages set forth, that the foregoing description and the drawings are illustrative and not limiting, and that the spirit and scope of the present invention are to be determined by reference to the appended claims.

What is claimed is:

1. An endotracheal tube holder, comprising:
    a support member including means adapted to be placed over, and upwardly supported by, the nose of the patient;
    attachment means for attaching said support member to the patient's face, holding said support member firmly in place against the patient's nose and providing lateral support to said support member,
    a tube holder member adapted to firmly engage and hold in place an intubated endotracheal tube;
    connecting means providing rigid mechanical support between said support member and said tube holder member such that said tube holder member is positioned immediately in front of the patient's mouth when said support member is emplaced over the patient's nose;
    said attachment means includes a main strap adapted to extend around the back of a patient's head, the two ends of said main strap being attached to either side of said support member, whereby said support member is maintained in place, and two supplemental straps, one end of each supplemental strap being attached to said connecting means, the opposite ends of each supplemental strap being further connected at positions along said main strap on opposite sides of said support member, whereby said support member is maintained in place.

2. An endotracheal tube holder as recited in claim 1, wherein said support member comprises a thin contoured plate shaped to fit over the patient's nose, having openings providing air flow for the nostrils.

3. An endotracheal tube holder as recited in claim 2, wherein said thin contoured plate is further provided with a thin layer of soft absorbent material attached to and lining its inner surface, whereby said layer is in contact with the patient's nose.

4. An endotracheal tube holder as recited in claim 1, wherein said main strap and said supplemental straps are constructed out of elastic material.

5. An endotracheal tube holder as recited in claim 1, wherein said connecting means includes a connecting member extending directly from said support member at the lower extremity of the patient's nasal septum to said tube holder member at the patient's upper lip.

6. An endotracheal tube holder as recited in claim 1, wherein said tube holder member includes a semi-tubular channel having a tubular axis, oriented such that the tubular axis is directed toward the patient's mouth, with a lateral opening extending from end to end of the channel, permitting insertion and removal of an endotracheal tube through said opening by moving the tube in a direction transverse to the tubular axis.

7. An endotracheal tube holder as recited in claim 6, wherein said tube holder member is constructed out of resilient plastic material.

8. An endotracheal tube holder comprising:

a support member including means adapted to be placed over, and upwardly supported by, the nose of the patient;

a tube holder member adapted to firmly engage and hold in place an intubated endotracheal tube;

a connecting member connected between said support member and tube holder and extending directly from said support member at the lower extremity of the patient's nasal septum to said tube holder member at the patient's upper lip, such that said tube holder member is positioned immediately in front of the patient's mouth when said support member is emplaced over the patient's nose;

a main strap extending around the back of the patient's head, the two ends of said main strap being attached to either side of said support member, whereby said support member is maintained in place; and two supplemental straps, one end of each supplemental strap being attached to said connecting member, the opposite ends of each supplemental strap being further connected at positions along said main strap on opposite sides of said support member, whereby said connecting member is maintained in place.

9. An endotracheal tube holder as recited in claim 8, wherein said main strap and said supplemental straps are constructed out of elastic material.

10. An endotracheal tube holder as recited in claim 9, wherein said supplemental straps are connected to said main strap by passing through small constricting openings in said main strap and being squeezed and frictionally secured at the point of said openings, such that said supplemental straps may be tightened by pulling them through said openings.

* * * * *